US009328321B2

(12) United States Patent
Farotto (10) Patent No.: US 9,328,321 B2
(45) Date of Patent: May 3, 2016

(54) MAGNETIC SUSPENSION DENSITY MEASURING DEVICE FOR USE IN HOSTILE ENVIRONMENT, AND RELATED OPERATING METHOD

(71) Applicant: Carlo Farotto, Conzano (IT)

(72) Inventor: Carlo Farotto, Conzano (IT)

( * ) Notice: Subject to any disclaimer, the term of this patent is extended or adjusted under 35 U.S.C. 154(b) by 476 days.

(21) Appl. No.: 13/965,882

(22) Filed: Aug. 13, 2013

(65) Prior Publication Data

US 2014/0157992 A1     Jun. 12, 2014

(30) Foreign Application Priority Data

Aug. 14, 2012 (IT) .............................. TO2012A0728

(51) Int. Cl.
*G01N 9/14* (2006.01)
*C12G 1/02* (2006.01)
*G01N 9/12* (2006.01)

(52) U.S. Cl.
CPC .. *C12G 1/02* (2013.01); *G01N 9/12* (2013.01); *G01N 9/14* (2013.01)

(58) Field of Classification Search
CPC ....................................................... G01N 9/14
USPC ............................................................ 73/453
See application file for complete search history.

(56) References Cited

U.S. PATENT DOCUMENTS

| 1,491,487 | A |   | 4/1924  | Means |               |
|-----------|---|---|---------|-----------|-----------|
| 2,958,224 | A | * | 11/1960 | Edelmann  | G01N 9/14 |
|           |   |   |         |           | 73/442    |
| 3,631,727 | A | * | 1/1972  | White     | G01N 9/14 |
|           |   |   |         |           | 73/440    |
| 4,422,085 | A | * | 12/1983 | Sumitomo  | B41J 2/195|
|           |   |   |         |           | 137/91    |
| 4,720,998 | A | * | 1/1988  | Hogue     | G01N 9/12 |
|           |   |   |         |           | 366/140   |
| 5,900,547 | A | * | 5/1999  | Bartkiewicz | G01N 9/18 |
|           |   |   |         |           | 73/32 R   |
| 7,416,642 | B2| * | 8/2008  | Nadeau    | B01D 1/305|
|           |   |   |         |           | 159/18    |

FOREIGN PATENT DOCUMENTS

FR           2563339         10/1985
WO      WO 2011/058585        5/2011

* cited by examiner

*Primary Examiner* — Lisa Caputo
*Assistant Examiner* — Jamel Williams
(74) *Attorney, Agent, or Firm* — Leason Ellis LLP (57) ABSTRACT

A density measuring device is described having: a housing, internally defining a first chamber, designed to contain a fluid the density of which it is desired to measure, and housing, in a measurement operating condition, a float, designed to be immersed in the fluid; and an electronic circuit that detects a value of the density as a function of a thrust sustained by the float due to the effect of the fluid; the housing further defines a second chamber, designed to contain a filling gas and to house the float in a cleaning operating condition of the float, distinct from the measurement operating condition, for removing gas bubbles and/or solid particles that have adhered to an outer surface of the float during the measurement operating condition.

16 Claims, 6 Drawing Sheets

MAGNETIC SUSPENSION DENSITY MEASURING DEVICE FOR USE IN HOSTILE ENVIRONMENT, AND RELATED OPERATING METHOD

The present invention relates to a magnetic suspension density measuring device for use in hostile environments and a related operating method; in particular, the following discussion will make explicit reference, without any loss of generality, to use of the measuring device in a wine-making environment, in the field of a wine-making process.

BACKGROUND OF THE INVENTION

In the last few years, significant advances have been made in management and control of wine-making, intended as the set of operations that contribute to the production of a wine through alcoholic fermentation of an initial liquid-solid mixture, must or pressed grapes.

For example, wine-making tanks have been conceived with automatic systems of pumping over and temperature control, with the possibility of heating or cooling, controlled with the aid of processing units that acquire data coming from several sensors arranged on board the tanks, able to detect, for example, the density of the must, the mass flow of the carbon dioxide ($CO_2$) generated, the temperature of the must, etc. These systems enable the user to monitor the fermentation process and to manually adjust the wine-making parameters (including an increase and/or drop in temperature, the addition of nutrients, the operation of pumps and mechanical mixing actuators for the must, etc.).

In particular, in patent application WO 2011/058585, an automated wine-making system has been proposed that envisages processing, by means of a suitably trained neural network, a collection of historical data regarding past wine-making processes, stored methodically and systematically in a database, in order to obtain, by means of a data mining process, an optimal wine-making model, optimized for the characteristics and conditions peculiar to the wine-making process that is to be carried out. The system also envisages management and control of the wine-making process during its execution on the basis of the previously developed optimized model, by using a suitable artificial intelligence unit, in particular one implementing fuzzy logic algorithms, able to implement self-learning and adjustment operations referring to the optimized model in order to prevent/avoid/attempt to resolve possible anomalies of the fermentation kinetics, both automatically and by issuing alarms and work orders to operators. The same system envisages enlarging the above-mentioned database at the end of each wine-making process by using the information collected during execution of the same wine-making process and any other information considered useful (even if collected later on), so as to augment the content of the database in a continuous manner and consequently optimize the wine-making models, which will be subsequently developed starting from this database, being increasingly accurate and reliable.

The above-mentioned automated wine-making system also bases part of its operation, in particular regarding the control of the wine-making process as a function of the developed optimized model, on the data collected in the field by suitable sensors, including a fermentation mixture density sensor.

One problem that afflicts this system and, in general, solutions for automating the wine-making process that envisage real-time control of the fermentation mixture's conditions, is without doubt linked to the hostile conditions that arise inside the wine-making tanks during the course of fermentation.

It is well known that the raw material to be processed (pressed grapes) is a fluid mixture composed of many chemical components of both vegetable (sugars, acids, organic salts, etc.) and chemical (pesticides and fertilizers) origin, in which solid parts (of very variable size, ranging from specks of dust to parts of a few millimeters in size) are found in suspension, with adhesive properties (due to the sugars) and highly variable viscosity, which may reach very high values (up to having a gelatinous consistency). In general, it is known that this mixture may give rise to deposits due to the growth of salt crystals, as well as the growth of organic masses (moulds and bacterial colonies).

In this regard, Sablayrolles, J. M. "Control of alcoholic fermentation in winemaking: Current Situation and prospect", Food Research International, 2009, although pointing out the advantages offered in principle by the real-time control of the fermentation process through use of suitable sensors (including, in particular, a density sensor for control of the fermentation curve or rate), underlines the fact that the technology available in the sensor field is generally found to be incompatible with the wine-making environment.

In particular, density sensors are known that exploit the buoyancy that acts on a movable float to detect the density of the fluid in which the float is at least partially immersed.

For example, patent application FR-A1-2 563 339 discloses a magnetic suspension densimeter in which the float is partially submerged in a liquid for which it is desired to measure the density and it is suitably kept in suspension by the action of an electromagnet and a position control loop.

However, density sensors using pressure sensors or exploiting the buoyancy that acts on a movable float (including magnetic suspension densimeters), or still are based on reflectometry, are heavily disturbed by the type of liquid to be measured; measurement becomes substantially unreliable if they are then left in contact with the liquid to be measured for long periods of time (days or weeks), as is instead required for real-time fermentation process monitoring applications.

For example, S. K. Singh "Industrial Instrumentation and Control", McGraw Hill, 2008, page 253, considers magnetic suspension densimeters unsuitable for working in soiled and deposit-forming fluids.

Thus, the need is definitely felt, especially in the wine-making sector, for measuring instruments better suited to the hostile environments in which they are used, so as to allow effective implementation of the desired methods of process automation.

SUMMARY OF THE INVENTION

The aim of the present invention is to at least partially solve the previously indicated problems and satisfy the above-stated need, and, in particular, to provide a density measuring device that has greater insensitivity to hostile operating environments and that therefore enables, for example, implementing an accurate and reliable automated control system for the fermentation process inside a wine-making tank.

According to the present invention, a density measuring device and an associated method of operation are provided, as defined in the appended claims.

BRIEF DESCRIPTION OF THE DRAWINGS

For a better understanding of the present invention, some preferred embodiments will now be described, purely by way of non-limitative example and with reference to attached drawings, where.

DETAILED DESCRIPTION OF THE INVENTION

The present invention originates from in-depth research carried out by the Applicant regarding the hostile conditions that arise inside a wine-making tank during the process of alcoholic fermentation of the initial liquid-solid mixture, the must or pressed grapes.

In particular, the Applicant has identified an as yet undocumented problem related to the use of a magnetic suspension density measuring device in the above-mentioned hostile conditions inside the wine-making tank.

During the fermentation phase, the mixture inside the tank becomes a solution supersaturated with $CO_2$ gas (produced by the fermentation), giving rise to a two-phase liquid-gas solution and the consequent generation of a considerable quantity of gas bubbles suspended in the liquid. In the case of using a magnetic suspension density measuring device, which, as is known, is based on the application of the principle of Archimedes to a floating body immersed in the fluid for which it is desired to determine the density, these bubbles stick to the floating body by surface adhesion, producing a change in the force acting thereon, by increasing the volume and consequently the magnitude of the buoyancy to which the body is subjected. A systematic error is thus caused in the density value detected by the measuring device, the size of which becomes larger the longer the floating body remains immersed in the gas-supersaturated liquid (given that the accumulation of gas bubbles continues to grow), until the measurements performed effectively become useless.

Figure 1:
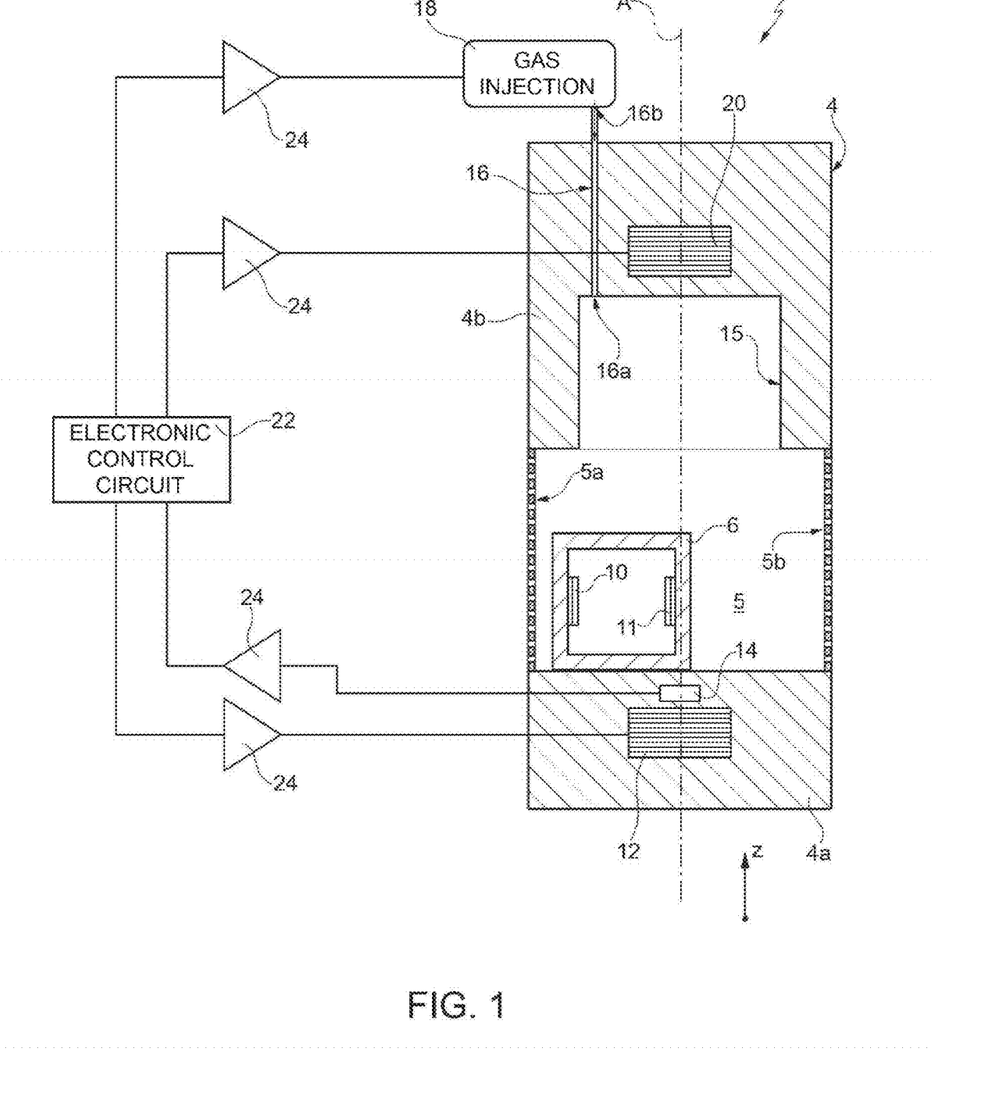
FIG. 1 shows a schematic representation of a magnetic suspension density measuring device, according to one embodiment of the present invention, in a first operating condition.
Figure 2:
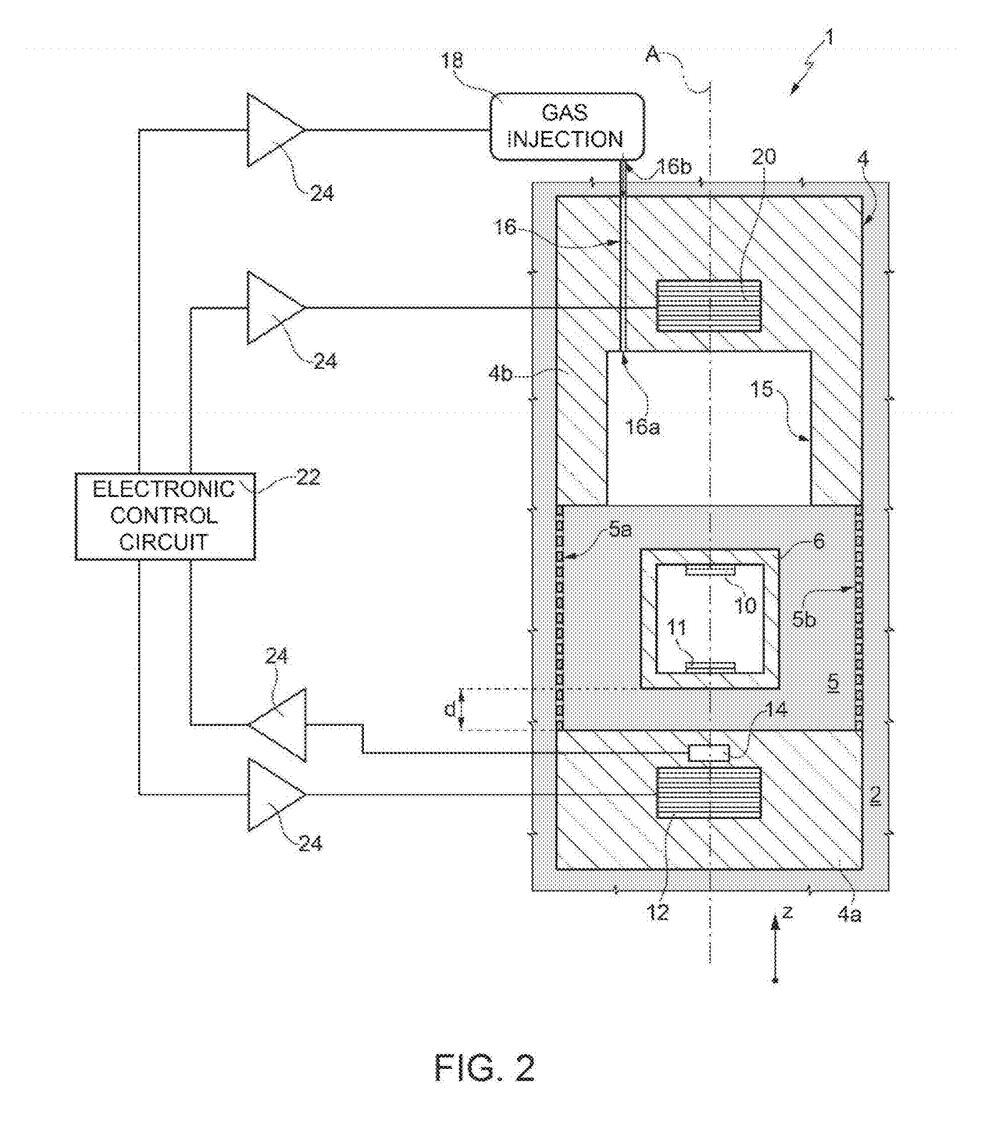
FIG. 2 shows a schematic representation of the density measuring device of FIG. 1, in a second operating condition.

With reference to FIGS. 1 and 2, a density measuring device of the magnetic suspension type, indicated in general by reference numeral 1 and that is intended to solve the above-discussed problems will now be described. In FIG. 1, the density measuring device 1 is shown in a non-operating condition (so-called "empty"), while in FIG. 2, the density measuring device 1 is shown in a measurement operating condition, immersed in a fluid 2 under test for which a density measurement is required, for example, pressed grapes inside a fermentation tank (not shown here).

The density measuring device 1 comprises a measuring housing 4, having, for example, an elongated cylindrical shape, preferably of miniaturized size, for example with a diameter of less than 49 mm, to allow its insertion inside the fermentation tank, for example, through a ball valve with an effective entrance diameter of 49 mm (corresponding to a valve with the name DIN/MACON/GAROLLA 50/60, commonly used in the alcohol fermentation sector). The measuring housing 4 is therefore insertable in the fermentation tank and removable therefrom for routine and unplanned maintenance and for conservation at the end of the fermentation cycle, in a suitable location for preserving reliability (soaking in an inert, descaling and disinfectant solution).

The density measuring device 1 has, inside the measuring housing 4, for example in its lower half (with respect to a normal measuring position), a measuring chamber 5 designed to be filled with the fluid 2 and internally housing a float 6.

The measuring housing 4 has an axis of symmetry A, arranged, in the measuring position, parallel to a vertical axis z.

In particular, the measuring chamber 5 is laterally defined by wall portions 5a and 5b, which also define a portion of the side wall of the measuring housing 4, shaped as a grating, or grill, so that the fluid 2 can pass through it when the measuring device 1 is at least partially immersed in the fluid 2, i.e. in a measurement operating condition. The same wall portions 5a and 5b also laterally contain the float 6 inside the measuring chamber 5 when the density measuring device 1 is not immersed in the fluid 2, i.e. in the non-operating condition (in which, as shown in FIG. 1, the float 6 rests on a base portion 4a of the measuring housing 4, with the density measuring device 1 in the vertical position). The measuring chamber 5 is also delimited at the bottom (with respect to the vertical axis z) by the same base portion 4a of the measuring housing 4.

The float 6 internally includes two permanent magnets 10, 11, with opposing magnetic fields that, due to their physically opposite positions, reduce the force of the overall magnetic field of the float so as to make it less sensitive to the action of external magnetic fields, which could disturb the measurement. For example, the float 6 is formed by a generically parallelepipedal, internally hollow body, and the permanent magnets 10 and 11 are connected to internally opposite walls of this hollow body, so that they are facing each other.

The density measuring device 1 comprises a suspension solenoid 12, housed in the base portion 4a of the measuring housing 4, at the axis of symmetry A, so as to generate, when electrically powered, a magnetic field inside the measuring chamber 5, able to interact with the pair of permanent magnets 10 and 11 of the float 6. As will be described in detail hereinafter, during the measuring phase, the suspension solenoid 12, when suitably controlled, enables keeping the float 6 suspended at a certain predetermined reference distance d from the base portion 4a of the measuring housing 4 (measured along the vertical direction z), by suitably varying the force of the generated magnetic field.

The density measuring device 1 further comprises, again housed in the base portion 4a, close to the suspension solenoid 12 and at the axis of symmetry A, a position measuring device 14, in particular a Hall-effect measuring device (of a known type, not described in detail herein), which enables, in the measurement operating condition, the indirect reading of the distance of the float 6 suspended in the fluid 2 from the base portion 4a, by measuring the intensity of the magnetic field due to interaction with the float 6.

According to a particular aspect of the present invention, a cleaning chamber 15 is obtained in an upper portion 4b of the measuring housing 4, arranged on the opposite side from the base portion 4a with respect to the measuring chamber 5 along the vertical axis z, such that it faces the measuring chamber 5. For example, the upper portion 4b of the measuring housing has an inverted U shape in section and the cleaning chamber 15 defines a cavity obtained in this upper portion 4b, delimited laterally and at the top by the measuring housing 4 and in direct fluidic communication with the measuring chamber 5. A tubular conduit 16 passes through the upper portion 4b of the measuring housing 4, and has a first end 16a in communication with the cleaning chamber 15 and a second end 16b connected to a gas injection device 18 (shown schematically and, for example, including a porous candle for supplying oxygen). As will be described in detail hereinafter, the gas injection device 18 is controlled so as to fill the inside of the cleaning chamber 15 with a gas, for example oxygen ($O_2$) in the gas phase, coming from an external depot to the wine-making tank (not shown), particularly when fermentation is not in progress; instead, when fermentation is in progress, the cleaning chamber 15 is independently fed with $CO_2$ coming from the fermentation process (the $CO_2$, produced in the form of small bubbles by the fermentation of the must, a phenomenon in wine-making also known as 'perlage', remains trapped in the cleaning chamber 15, as the axis of symmetry A is kept parallel to the vertical axis z, perpendicular to the ground).

The density measuring device 1 further comprises, housed in the upper portion 4b of the measuring housing 4, close to and above the cleaning chamber 15 and at the axis of symmetry A, a return solenoid 20, such as to generate, when electrically powered, a magnetic field able to interact with the pair of permanent magnets 10 and 11 of the float 6. As will be described in detail hereinafter, the return solenoid 20, when suitably controlled, enables attracting the float 6, and in particular ensuring that the float 6 emerges from the fluid 2 in the measuring chamber 5 and enters the cleaning chamber 15.

Figure 3:
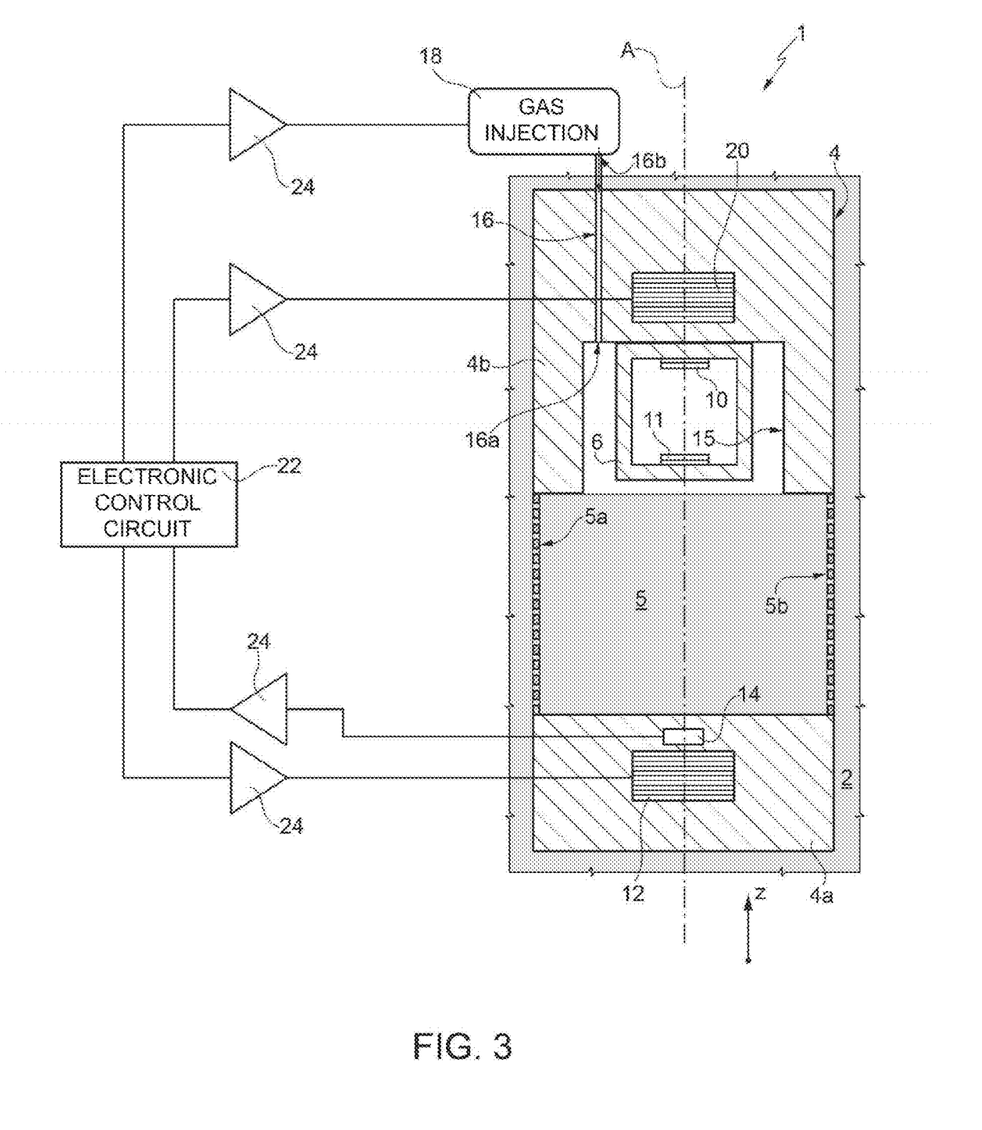
FIG. 3 shows a schematic representation of the density measuring device of FIG. 1, in a third operating condition.

In particular, as shown in FIG. 3, in the cleaning operating condition, the float 6 is completely housed in the cleaning chamber 15, being arranged in contact with the upper surface of the cleaning chamber 15.

The suspension solenoid 12, the float 6 and the return solenoid 20 are also vertically aligned along the axis of symmetry A in the measurement (FIG. 2) and cleaning (FIG. 3) operating conditions.

In particular, during operation, the positioning of the permanent magnets 10 and 11 at the top and bottom ends of the float 6 reduces the effective distance from the return solenoid 20 and the suspension solenoid 12, respectively, to a minimum, allowing the overall miniaturization of the density measuring device 1 (as previously indicated).

The density measuring device 1 further comprises an electronic control circuit 22, shown schematically, arranged externally to the measuring housing 4 and the wine-making tank (in the exemplary use in the wine-making field), and suitably electrically connected (by the interposition of respective drivers 24) to the suspension solenoid 12, the return solenoid 20, the position sensor 14 and the gas injection device 18. In particular, in a manner not shown, the electronic control circuit 22 comprises a processing unit (for example a microprocessor or a microcontroller), a display for displaying the data readings regarding the density value of the fluid 2 and a user interface.

Figure 4:
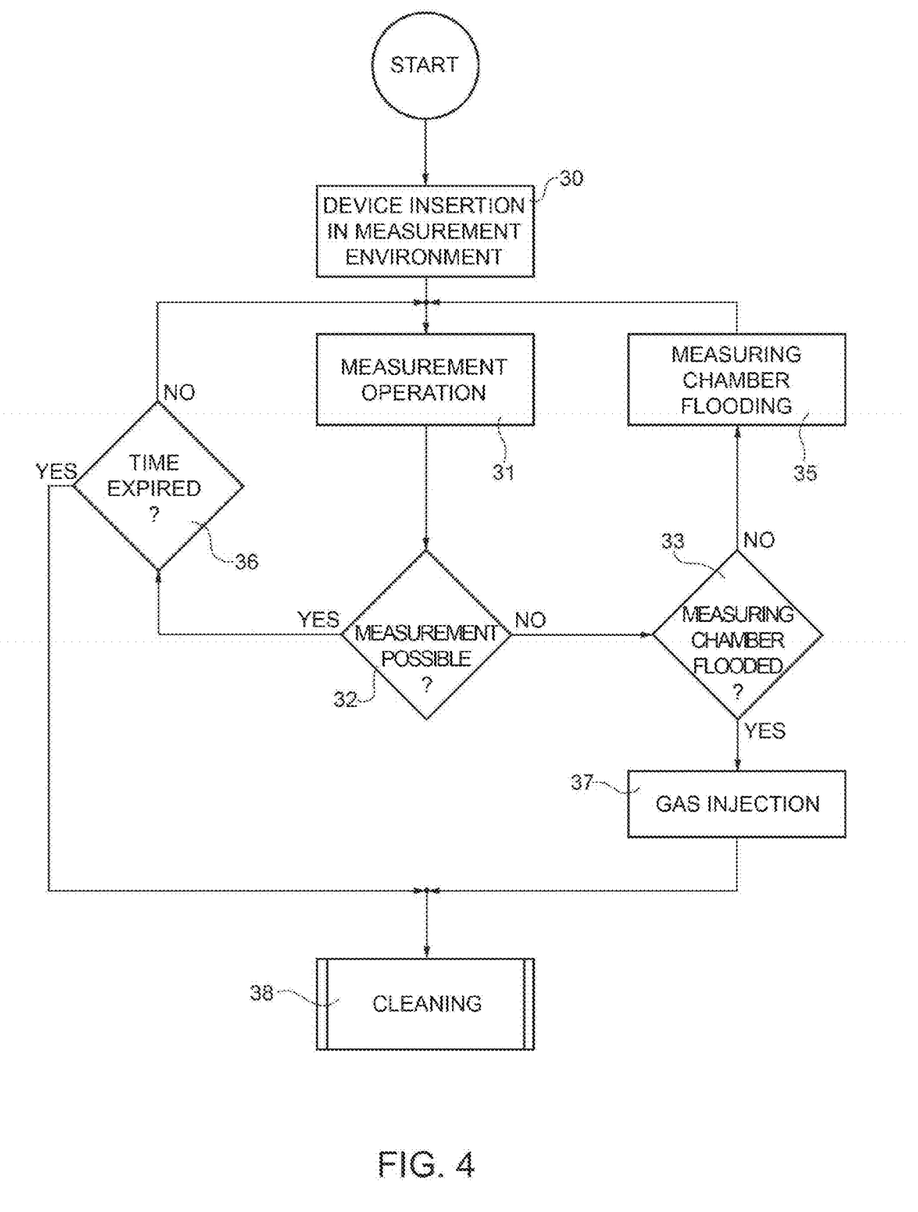
FIGS. 4 and 5 show flowcharts regarding a method of operation of the density measuring device in FIG. 1.

The operation of the density measuring device 1 will now be described, initially with reference to FIG. 4.

In an initial step, indicated by reference numeral 30, the measuring housing 4 is inserted into the measurement environment suitable for storing the fluid, 2 the density of which it is desired to measure, for example inside a wine-making tank. In particular, the housing 4 is inserted keeping the axis of symmetry A perpendicular to the ground (parallel to the vertical axis z), so as to preserve a given amount of gas (air) inside the cleaning chamber 15, this gas being required for immediate operation of the density measuring device 1, even when there is no fermentation and with the gas injection device 18 not in operation, and so as to enable when fermentation is in process, as already mentioned, self-feeding of the cleaning chamber 15 with $CO_2$ fermentation gas (in wine-making, a phenomenon known as 'perlage').

The electronic control circuit 22 operates, electrically powering the suspension solenoid 12, which tends to attract the float 6, and reads, via the position sensor 14, the distance of the float 6 from the base portion 4a of the housing 4, step 31.

When inserting the housing 4 with the fermentation tank empty, the float 6 (FIG. 1) is free to move inside the housing 4, contained by the wall portions 5a and 5b, with no upward thrust force being exerted (due to the principle of Archimedes), given that no fluid is yet present inside the measuring chamber 5. Reading the density value in this phase is not meaningful and measuring the density is not possible, step 32, and so a corresponding indication for the user (for example, the message "OFF") is displayed on the display of the electronic control circuit 22. In particular, this indication informs that the measuring chamber is not flooded, step 33.

The subsequent filling of the fermentation tank with must or pressed grapes, allows flooding the measuring chamber 5 with part of the fermentable fluid 2, step 35.

Measurement operations on the density of the fluid 2 are then carried out, as measuring the density is possible in this situation (steps 31 and 32).

In the measurement condition, the float 6, due to the buoyancy effect, tends to rise upwards (i.e. it moves away from the base portion 4a), as it is designed to be lighter than the fluid 2, but it is held at a predetermined distance d by the suspension solenoid 12 powered by the electronic control circuit 22. In particular, the electronic control circuit 22 implements a feedback control loop, based on the values detected by position sensor 14, to adjust the electric current running through the suspension solenoid 12 to the value required for keeping the distance of the float 6 from the base portion 4a constant.

When the float is in the measuring position (position shown in FIG. 2), at the predetermined distance d from the base portion 4a (arranged substantially in a central position with respect to the measuring chamber 5), the value of the current that runs through the suspension solenoid 12 is proportional to the value of the density of the fluid 2 present in the measuring chamber 5. This density value is conveniently shown on the display of the electronic control circuit 22 located outside the fermentation tank and stored and/or sent to other processing systems for further processing operations.

In particular, to avoid the measures by the position measuring device 14 being disturbed by the magnetic field generated by the suspension solenoid 12 (which is positioned close to the position measuring device 14 to allow the miniaturization of the density measuring device 1), the electronic control circuit 22 provides a procedure to cancel this magnetic interaction. At regular intervals, the suspension solenoid 12 is deactivated for a very short time (to avoid the float 6 perceptibly changing position during this micro-interruption of the force holding it). Immediately after switching off the driver 24 that controls the suspension solenoid 12, there is a brief pause to wait for the magnetic flux to completely dissipate. When the magnetic flux of the suspension solenoid 12 completely disappears, it is possible to read the position of the float accurately via the position sensor 14.

As the fermentation proceeds, due to the capillarity phenomena and surface adhesion between the fermenting gas-supersaturated liquid (forming small gas bubbles, called 'perlage' in wine-making) and a solid body, hydrophobic due to the presence of surface roughness from manufacture (the float 6), the float 6 becomes covered with a plurality of fermentation gas bubbles that alter the volume and consequently the apparent specific weight, changing the density reading provided by the density measuring device 1 and rendering it unreliable.

To obviate this (which should be stressed, is a technical problem identified by the Applicant through in-depth research and not known to the average technician in the wine-making machinery sector), one aspect of the present invention envisages the execution, at predetermined time intervals, of a cleaning cycle of the float 6, for removing the bubbles that have adhered to it by capillarity and surface adhesion.

In particular, the electronic control circuit 22 checks whether a predetermined time interval has elapsed since the last cleaning cycle, step 36, and, if so, starts a new cleaning cycle, step 38.

Figure 5:
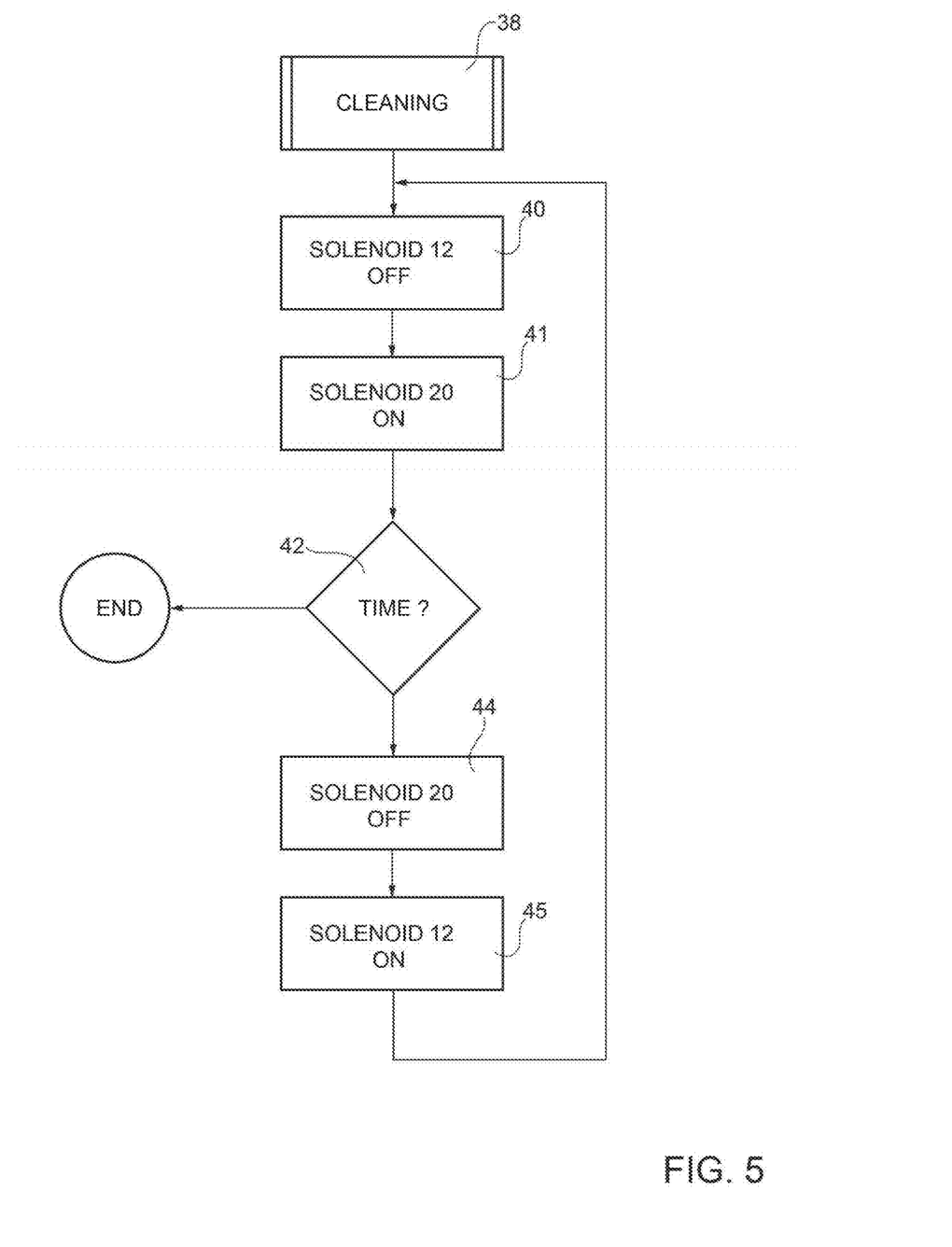

As shown in detail in FIG. 5, first of all this cleaning cycle interrupts the action of the suspension solenoid 12, step 40, and activates the return solenoid 20, step 41.

In this way, the float 6 is attracted upwards and enters the cleaning chamber 15 full of gas (position shown in FIG. 3), moving until it contacts the upper wall of the cleaning chamber 15: the impact and consequent rapid outflow of the liquid induces its cleaning by shaking, which allows cleaning the float of the deposits that were deposited on its surface. In addition, by the float being inside the cleaning chamber 15 full of gas, it is also freed of the fermentation gas bubbles that formed on its surface due to surface adhesion when it was immersed in the fermenting fluid 2 in the measuring phase.

The process of the fermentation of the mixture inside the wine-making tank, a notoriously encrusting environment, entails solid organic and polluting particles being deposited on the float 6, these also destined to alter the correct reading of the density and also cause the clogging/jamming of moving parts of the density measuring device 1. The cleaning cycle advantageously provides for removing these clogging/jamming particles as well (by means of the above-mentioned mechanism of cleaning by shaking), restoring correct operation of the density measuring device 1.

In particular, in step 42, the electronic control circuit 22 checks whether a predetermined period scheduled for the cleaning cycle has elapsed; if this is not the case, the electronic control circuit 22 deactivates the return solenoid 20, step 44, and, in sequence, reactivates the suspension solenoid 12, step 45, in this way attracting the float 6 downwards again, into the measuring chamber 5.

The process then returns to step 40, with the electronic control circuit 22 inverting the activation and deactivation commands for the suspension and return solenoids 12 and 20 again, so as to attract the float 6 upwards.

These operations are repeated a number of times (until the end of the time interval dedicated to the cleaning cycle), in this way carrying out the cleaning of the float 6 by shaking off the encrusting particles deposited on its surface during the measurement cycle.

Once the cleaning cycle ends, the float 6 is released, permanently this time, so as to be immersed in the fermenting liquid and attracted by the suspension solenoid 12, in this way starting again a correct measurement of the density for a new measurement cycle.

The measurement cycle and the cleaning cycle thus mutually alternate, allowing high measurement accuracy for the density of the fermenting liquid to be achieved, for the entire duration of the fermentation process.

Instead, if it was not possible to keep the float 6 at the predetermined distance d during the measurement cycle, and therefore it was not possible to measure the density, as checked for again in step 32, the message "DIRTY" would be displayed on the display associated with the electronic control circuit 22, indicating that, as in this situation the measuring chamber 5 is flooded, as checked for again in step 33, the system anomaly is due to a possible inefficiency of the cleaning system and therefore, in a first hypothesis, to a probable lack of gas inside the cleaning chamber 15. Possible drops in the filling level of the cleaning chamber 15 may be due, for example, to bad positioning of the housing 4 in the insertion step, to the fermentation halting, or accidental gas leakage from the cleaning chamber 15.

The electronic control circuit 22 then controls the injection of a quantity of gas into the cleaning chamber 15, to resolve the anomaly, before executing a subsequent cleaning cycle, step 37.

In the case where the electronic control circuit 22 records a certain number (set in the design phase) of "DIRTY" events within a certain predetermined period of time, it finally halts, showing a "FAILURE" message on the display and needs to be serviced by a specialized technical support engineer.

The advantages of the density sensor and the related operating method are clear from the foregoing description.

In any case, it is underlined again that the above-mentioned alternating of the measurement and cleaning cycles, by means of suitable electrical commands given by the electronic control circuit 22 to the suspension and return solenoids 12, 20, enables removing the gas bubbles from the float 6 that form on its surface due to surface tension and, at the same time, avoids/eliminates any deposits of encrusting and/or jamming and/or clogging substances on its surface (because of the cleaning by shaking).

The density measurement provided by the density measuring device 1 is therefore extremely reliable, even over long periods of measurement, as required, for example, for continuous, real-time fermentation mixture monitoring.

Furthermore, the miniaturization of the density measuring device 1, made possible by its structure, allows mounting it on a rod for removable insertion in the measurement environment, that is, for example, a wine-making tank. This possibility of removal allows resolving a specific technical problem in making red wines, which provides for, when fermentation is completed, the so-called racking off, or rather the drawing off of the liquid part from the tank. During this operation, the so-called marc cap, which floats on the surface in the wine-making tank, descends, and as it is thick and compact, can hit and damage any part projecting from the inner wall of the tank (just like the density sensor if it has not been opportunely removed from the tank beforehand). The possibility of removing the density measuring device 1 therefore avoids having to provide a protective structure (such as a cover, for example) for installation inside the wine-making tank.

Figure 6:
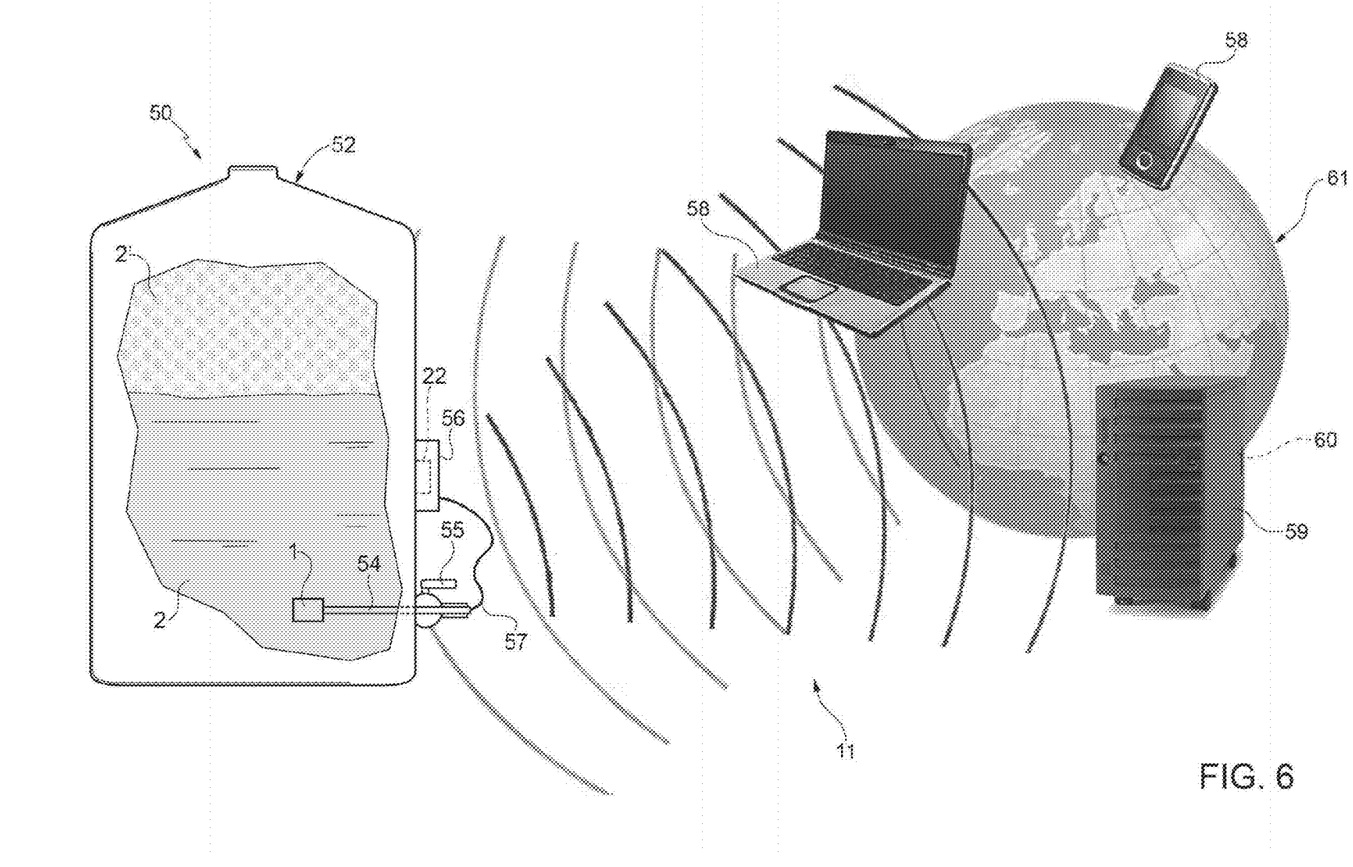
FIG. 6 is a block diagram of an automated wine-making system using the density measuring device of FIG. 1.

The application of the density measuring device 1 is therefore exceedingly advantageous in an automated control system for the wine-making process, as schematically shown in FIG. 6 (and as described in detail in the above-mentioned patent application WO 2011/058585).

In particular, the automated control system, indicated by reference numeral 50, comprises:
  a wine-making tank 52, suitable for containing a liquid-solid mass (the must or pressed grapes) subjected, during the wine-making process, to maceration/fermentation for its transformation into wine, and in particular the fluid 2 for which it is desired to measure the density (on the surface of which a solid layer may be present, the so-called marc cap, indicated here by reference numeral 2');
  a plurality of sensors, operatively connected to the wine-making tank 52, suitable for detecting a plurality of quantities relevant for the wine-making process and including, among others, a temperature sensor, a pressure sensor, a mass flow sensor and, in particular, the density measuring device 1 previously described in detail, in this case carried by a rod 54, which is inserted inside the wine-making tank 52 through a valve 55, for example, a ball valve with an effective entry diameter of 49 mm;

a plurality of actuators, which are operable to control the processing of the mixture, including: an automatic wine-making robot (or robot arm), capable of carrying out operations of light spraying, classic pumping over and vigorous punching the cap (or "sinking"); a suction conduit associated with a pump for pumping over the mixture, with the function of sucking part of the mixture from a lower portion of the wine-making tank 52 and transferring it to an upper portion of the same tank, so as to remix the mixture; a metering pump for nutrients, antioxidants and other additives; a porous diffuser for blowing oxygen ($O_2$) and an associated metering chamber; a first coil to provide heat and increase the temperature of the mixture; and a second coil to provide cold and decrease the temperature of the mixture;

a control unit 56, for example, of the microprocessor type, connected to the wine-making tank 52 (for example, being arranged on board the tank), and operatively connected both to the sensors, especially the density measuring device 1 (including the electronic control circuit 22), to receive signals related to the physical quantities regarding the wine-making process via an electric cable 57, and to the actuators, so as to drive these actuators, on the basis of the sensor output data and suitable processing (in particular, executed using fuzzy logic algorithms), to implement suitable corrective actions on the wine-making process and/or activate suitable alarm warnings; in particular, the control unit 56 executes a dedicated program and a set of software instructions in order to check that the wine-making process follows a particular optimized wine-making model that has been received and stored in an associated memory beforehand;

a local processing unit 58, for example, in the form of a portable computer (laptop), palmtop or smart-phone, which communicates and performs data exchange with the control unit 56, in a wired manner or preferable in a wireless manner (for example via Wi-Fi, Bluetooth or IR transmission) and/or via an Ethernet connection to a local network (intranet), and, in particular, transmits the optimized wine-making model to the control unit 56 before starting the wine-making process, and receives output data from the control unit 56 regarding the wine-making process, during the execution and at the end of the wine-making process;

a central processing unit 59, in particular including an intranet server and/or an internet server that can be used on-demand and supports SaaS (Software as a Service), equipped with a memory suitable for containing a wine-making database 60, storing historical data regarding past wine-making processes to be used as reference data for the wine-making process to be undertaken, and able to manage this wine-making database 60 and the logic for extracting optimized wine-making models from this database, through a suitable program and set of software instructions (in particular, by implementing a neural network); and suitable communications infrastructures 61 (using wireless, Wi-Fi, Bluetooth, IR, Ethernet and/or Internet technology) to enable data exchange between the control unit 56 on board the tank, the local processing unit 58 and the central processing unit 59; in particular, the local processing unit 58 accesses the central processing unit 59 wirelessly via an internet protocol, or via a local wireless or wired intranet network.

Finally, it is clear that modifications and variations may be made to what has been described and illustrated herein, without departing from the scope of the present invention, as defined in the appended claims.

In particular, although studied and optimized for use in the wine-making environment for controlling the wine-making process, it is evident that the previously-described density measuring device 1 can be advantageously applied to all those cases where a density measurement is required in a hostile environment, in which, for example, there is an encrusting fluid, with solid particles in suspension and/or gas supersaturation.

Furthermore, it is also evident that some components of the density measuring device 1 may differ from those shown in the previously-described exemplary embodiment; for example: the position sensor 14 could be an LVDT sensor, or operate according to electrostatic principles instead of the Hall effect; the arrangement of the cleaning chamber 15 and the suspension and return solenoids 12, 20 could be inverted with respect to the measuring chamber 5 along the vertical axis z (in particular, in the case where the float 6 was heavier than the fluid 2, instead of being lighter than the fluid 2, as in the previously illustrated case); the force exerted on the float 6 due to the principle of Archimedes could be measured by means of a balance, opportunely connected to the float 6, instead of being obtained indirectly from the value of the electric current supplied to the return solenoid 20 by means of the position control loop; or the float 6 could be kept in suspension and moved in a different manner with respect to electromagnetic actuation.

The invention claimed is:

1. A density measuring device (1), comprising: a housing (4), internally defining a first chamber (5), designed to contain a fluid (2) the density of which it is desired to measure, and housing, in a first measurement operating condition, a float (6), designed to be at least partially immersed into said fluid (2); and an electronic circuit (22), configured to detect a value of said density as a function of a thrust sustained by said float (6) due to the effect of said fluid (2), characterized in that said housing (4) further defines a second chamber (15), designed to contain a filling gas and to house said float (6) in a cleaning operating condition of said float (6), distinct from said measurement operating condition, for removing gas bubbles and/or solid particles that have adhered to an outer surface of said float (6) during said measurement operating condition.

2. The measuring device according to claim 1, wherein said float (6) carries at least a first magnet (11) and said housing (4) includes: a first solenoid (12), operable to magnetically interact with said float (6) in order to keep it suspended within said first chamber (5), during said first operating condition; and a second solenoid (20), operable to magnetically interact with said float (6) in order to attract it within said second chamber (15), during said second operating condition.

3. The measuring device according to claim 2, further comprising a position sensor (14), operable to detect a position of said float (6) with respect to a base portion (4a) of said housing (4) delimiting said first chamber (5); wherein said electronic circuit (22) is configured to implement a feedback control loop for keeping said float (6) at a predetermined distance (d) from said base portion (4a).

4. The measuring device according to claim 3, wherein said position sensor (14) is of the Hall-effect type and is arranged in the proximity of said first solenoid (12).

5. The measuring device according to claim 2, wherein said float (6) carries a second magnet (10), arranged with its magnetic field opposing that of said first magnet (11).

6. The measuring device according to claim 1, wherein said electronic circuit (22) is electrically coupled to said first (12) and second (20) solenoids and is configured to control the switching on, or off, of said first (12) and second (20) solenoids; wherein said electronic circuit (22) is configured to control the switching on of said first solenoid (12) and the switching off of said second solenoid (20) during said first operating condition; and to control the switching off of said first solenoid (12) and the switching on of said second solenoid (20) during said second operating condition.

7. The measuring device according to claim 6, wherein said electronic circuit (22) is configured to repeatedly control the alternate switching on and switching off of said first (12) and second (20) solenoids during said second operating condition, so as to cause an alternating movement of said float (6) between said first (5) and second (15) chambers.

8. The measuring device according to claim 1, wherein said second chamber (15) faces, and is in fluid communication with, said first chamber (5).

9. The measuring device according to claim 1, wherein said housing (4) is designed to be at least partially immersed in a measurement environment containing said fluid (2); and wherein said first chamber (5) is laterally defined by wall portions (5a and 5b) of said housing (4), said wall portions (5a and 5b) being shaped as a grating so that said fluid (2) passes therethrough, when said housing (4) is at least partially immersed in said measurement environment.

10. The measuring device according to claim 9, wherein said housing (4) has a miniaturized size and is configured for removable insertion into said measurement environment.

11. The measuring device according to claim 1, further comprising a gas injection device (18) including a conduit (16) that traverses a portion (4b) of said housing (4) and is in fluidic connection with said second chamber (15) for introduction of gas towards said second chamber (15).

12. An automated wine-making system (50), configured to control the execution of a wine-making process for the alcoholic fermentation of must obtained from a batch of grapes and the transformation thereof into wine in a wine-making tank (52), characterized by comprising: a density measuring device (1) according to claim 1, designed to be at least partially immersed into the must in said wine-making tank (52); and processing means (56, 58) configured to control actuating means designed to act on the must contained in said wine-making tank (52), as a function of a desired wine-making model and the density value of said must, detected in real time by said measuring device (1).

13. A method for operating a density measuring device (1) according to claim 1, comprising the steps of:
inserting said density measuring device (1) into a measurement environment, including said fluid (2) the density of which it is desired to measure; and
executing a measurement process of said density, during said first operating condition,
characterized by comprising the step, separate and different from said step of executing a measurement process, of executing a washing process of said float (6) during said second operating condition.

14. The method according to claim 13, wherein said step of executing a washing process is carried out after a predetermined time interval from the beginning of said measurement process.

15. The method according to claim 13, comprising cyclically and alternately repeating said steps of executing a measurement process and executing a washing process of said float (6).

16. The method according to claim 13, comprising the step of: controlling the introduction of an amount of said filling gas in said second chamber (15) according to the result of said step of executing a measurement process.

* * * * *